United States Patent
Kleffel et al.

(10) Patent No.: US 10,161,860 B2
(45) Date of Patent: Dec. 25, 2018

(54) FOG DETECTION METHOD

(71) Applicant: PREH GMBH, Bad Neustadt a. d. Saale (DE)

(72) Inventors: Thomas Kleffel, Höchberg (DE); Norbert Bauer, Bad Neustadt a. d. Saale (DE)

(73) Assignee: PREH GMBH, Bad Neustadt A. D. Saale (DE)

( * ) Notice: Subject to any disclaimer, the term of this patent is extended or adjusted under 35 U.S.C. 154(b) by 0 days.

(21) Appl. No.: 15/889,967

(22) Filed: Feb. 6, 2018

(65) Prior Publication Data
US 2018/0224372 A1 Aug. 9, 2018

(30) Foreign Application Priority Data
Feb. 8, 2017 (DE) .......... 10 2017 102 489

(51) Int. Cl.
| | |
|---|---|
| *G01N 21/53* | (2006.01) |
| *G01N 21/3554* | (2014.01) |
| *G08G 1/00* | (2006.01) |
| *G01S 17/02* | (2006.01) |
| *G01S 17/88* | (2006.01) |
| *G01W 1/00* | (2006.01) |
| *B60Q 5/00* | (2006.01) |
| *G08B 7/06* | (2006.01) |

(52) U.S. Cl.
CPC ......... *G01N 21/3554* (2013.01); *B60Q 5/005* (2013.01); *G01N 21/53* (2013.01); *G01S 17/02* (2013.01); *G01S 17/88* (2013.01); *G01W 1/00* (2013.01); *G08B 7/06* (2013.01)

(58) Field of Classification Search
CPC .... G01N 21/3554; G01N 21/53; G01S 17/02; G01S 17/88
USPC ......................................................... 340/901
See application file for complete search history.

(56) References Cited

U.S. PATENT DOCUMENTS

| | | | | |
|---|---|---|---|---|
| 4,636,643 A | * | 1/1987 | Nakamura | G01N 21/35 219/203 |
| 6,353,392 B1 | * | 3/2002 | Schofield | B60H 1/00785 318/444 |

(Continued)

FOREIGN PATENT DOCUMENTS

| | | |
|---|---|---|
| DE | 102010005012 A1 | 7/2011 |
| DE | 102010026800 A1 | 1/2012 |
| DE | 102013002683 A1 | 8/2014 |

*Primary Examiner* — John A Tweel, Jr.
(74) *Attorney, Agent, or Firm* — M&B IP Analysts, LLC

(57) ABSTRACT

The present disclosure relates to a fog detection method in a vehicle comprising the steps of: providing a first fog sensor with a first transmitter emitting a first encoded optical signal into a vehicle's surroundings, and an associated first receiver for receiving an optical signal reflected from the vehicle's surroundings, and a first analyzing unit for decoding, analyzing and providing a first detection result related to the reception, wherein, for encoding, a code is selected among a plurality of possible codes (A,B,C) by the first transmitter in a code selection, and the code selection is communicated from the first transmitter to the first receiver and/or the analyzing unit, wherein, upon analyzing the signal received from the first receiver by the first analyzing unit, the code selection is used for identifying the first encoded optical signal in the received signal.

11 Claims, 2 Drawing Sheets

(56) References Cited

U.S. PATENT DOCUMENTS

| | | | |
|---|---|---|---|
| 6,768,422 B2 * | 7/2004 | Schofield | B60H 1/00785 250/208.1 |
| 7,235,786 B2 * | 6/2007 | Bayha | G01N 21/538 250/339.11 |

* cited by examiner

FOG DETECTION METHOD

This application claims priority to the German Application No. 102017102489.1, filed Feb. 8, 2017, now pending, the contents of which are hereby incorporated by reference.

The present disclosure relates to a method for fog detection, as well as a system for fog detection. Known fog sensors comprise an optical transmitter and an associated optical receiver and are arranged to operate according to the principle of open light barrier. The optical transmitter is oriented such that the optical signal thereof is emitted into the vehicle surroundings, for example into the region located in front of the windshield and, in case of fog being present in this region, is reflected by back diffusion and is received by the transmitter. The detection of an optical signal reflected from the vehicle's surroundings through the receiver during eventually performed intensity analysis of the reflected signal finally results in confirmation of the presence of fog in the vehicle's surroundings and initiates deployment of a visual or acoustic warning message directed to the driver. With known fog detectors, there may be infiltration of extrinsic light, i.e. light from another fog sensor, thus resulting in accidental deployments and consequently in false alarms of the fog sensor receiving this extrinsic light. Moreover, the vehicle's surroundings to be detected by the fog sensor is limited due to limitation of transmission power of the transmitter.

In view of this background, there has been a need to provide a solution for a fog detection method having more reliable detection performance, the region to be monitored being comparably expanded, which especially may be realized at low-cost in a constructional point of view. This object will be solved by a method according to claim 1. An equally advantageous fog sensor as well as an appropriate system are the subject matter of each of the independent Claims. Advantageous embodiments are the subject matter of the respective dependent Claims. It is to be noted that the features, as individually set forth in the Claims, may be combined with each other in any technologically reasonable way and will point out further embodiments of the present disclosure. The description, especially in the context of the figures, additionally characterizes and specifies the present disclosure.

The present disclosure relates to a fog detection method in a vehicle comprising the following steps. In a providing step, a first fog sensor is provided. The fog sensor provided according to the present disclosure comprises a first transmitter and a first receiver. The first transmitter is formed to emit a first encoded optical signal into a vehicle's surroundings, whereas the first receiver is formed and disposed for receiving an optical signal reflected from the vehicle's surroundings. For example, reflection occurs if fog is present in the vehicle's surroundings. It is preferred for the first transmitter and the first receiver to be oriented such that the first receiver will be disposed exterior of the emission cone of the first emitter and thus, reception of the first signal by the first receiver exclusively occurs upon reflection in the vehicle's surroundings. Such an arrangement is also referred to as an "open light barrier". For example, the first transmitter and first receiver are arranged such that the main radiation direction of the first emitter and the main reception direction of the first receiver are oriented parallel to each other or intersect at an acute angle of preferably less than 45°, still more preferably less than 20°.

It is preferred for the vehicle's surroundings to be a region located in front of the windshield of the vehicle, extending a few decades of meters away from the vehicle. The light used is, for example, an infrared light. According to the present disclosure, the first fog sensor furthermore comprises a first analyzing unit for decoding, analyzing, and providing a detection result related to the reception. According to the present disclosure, in a code selection for encoding, a code is selected by the first transmitter among a plurality of possible codes, and the code selection is communicated from the first transmitter to the first receiver. In other words, the information, about which code has been selected by the first transmitter is communicated to the first receiver associated to the first fog sensor.

According to the present disclosure, upon analyzing the signal received by the first receiver by the first analyzing unit, code selection is used for identification of the first encoded optical signal in the receiving signal. I.e. information, which code among a plurality of codes is used on the first emitter side, is made use of in analyzing to discriminate the first optical signal from the other signals. It is for the person skilled in the art, to provide a sufficient number of different codes for sufficient diversification of the individual fog sensor among a plurality of fog sensors. By the measure according to the present disclosure, intrinsic reflection will more reliably be discriminated from extrinsic reflection or direct infiltration of an external fog sensor, thus more reliably avoiding erroneous detection of fog. In other words, due to knowledge of the intrinsic code, i.e. the signal emitted from the transmitter of the same fog sensor, discrimination thereof of that of another sensor is reliably allowed, and thus, verification of the detection result is allowed, to avoid erroneous detections of fog in such cases, where the optical signal of a second fog sensor is received by the first receiver of the first fog sensor. The first detection result initiates for example output of an optical or acoustic warning message to the driver.

According to another preferred embodiment of the method according to the present disclosure, in another providing step, a second fog sensor with a transmitter emitting a second encoded optical signal into the vehicle's surroundings is provided, wherein the code of the second encoded optical signal is selected among a plurality of possible codes through code selection. The second fog sensor provides a second detection result. In this embodiment, in a receiving step, the second encoded optical signal is received by the first receiver of the first fog sensor, and is decoded and analyzed by the first analyzing unit of the first fog sensor. The detection result of the first fog sensor is provided depending on the code selection of the second encoded optical signal. For example, upon receiving the second encoded optical signal, depending on the code selection thereof, the intrinsic original detection result, i.e. the detection result of the first analyzing unit, will be discarded upon additionally receiving the second signal. In this way, it simply is possible to affect the detection result of the first fog sensor by way of information that is located exterior of the vehicle's surroundings monitored by the first fog sensor.

It is preferred that code selection of the second encoded optical signal is done depending on the second detection result of the second fog sensor. It is preferred that detection results are assigned to specific fog conditions. As specific fog conditions, for example, positive detection of fog and non-detection of fog is understood. Moreover, supplemental fog conditions or detection results, respectively, specifying the above-mentioned detection results, such as detection of fog in a specified distance, may be provided. Due to dependence of code selection on the detection result or fog condition, respectively, it is possible to transmit detection results from one fog sensor to another fog sensor, and hence from one vehicle to another vehicle.

According to a preferred embodiment it is provided for the first analyzing unit to initiate output of an acoustic, haptic and/or optical warning message, in dependence of the code selection of the received second encoded optical signal, preferably a driver-directed warning message.

For example, the analyzing unit is configured to even output positive detection of fog as a first detection result, even if there is no first encoded optical signal to be received by the associated first receiver, but a second optical signal accordingly encoded, is received, i.e. a signal positively verifying the fog is received. In this way, a fog warning may be communicated from vehicle to vehicle, and early fog warning may be accomplished.

Preferably, at least the first encoded optical signal is encoded as a numerical sequence, still more preferably, the first and second encoded optical signals are encoded as a numerical sequence, for example as a pseudo random numerical sequence.

According to another embodiment, the second encoded optical signal comprises an instruction for the first receiver to cause intermediate interruption of transmission of the associated first transmitter. This is for example used to facilitate and/or to expand communication between the fog sensors.

The present disclosure relates to a fog sensor with a first transmitter emitting a first encoded optical signal into a vehicle's surroundings and an associated second optical receiver for receiving a signal reflected from the vehicle's surroundings, and a first analyzing unit for decoding, analyzing and providing a first detection result related to the reception. For encoding, a code is selected among a plurality of possible codes by the first transmitter in a code selection, and the code selection is communicated from the first transmitter to the first receiver. According to the present disclosure, in analyzing the signal received from the first receiver by the first analyzing unit, the code selection for identifying the first encoded optical signal is used in the received signal. By way of the configuration according to the present disclosure of the fog sensor, the intrinsic reflection will be discriminated more reliably from the extrinsic reflection or direct infiltration of an extrinsic fog sensor, thus more reliably avoiding erroneous detection of fog. In other words, due to knowledge of the intrinsic code, i.e. the signal emitted from the transmitter of the same fog sensor, discrimination thereof from that of another sensor is reliably allowed, and thus, verification of the detection result is allowed, to avoid erroneous detections of fog in such cases, where the optical signal of a second fog sensor is received by the first receiver of the first fog sensor. The first detection result, for example, initiates output of an optical or acoustic warning message to the driver.

The present disclosure furthermore relates to a system of the previously described first fog sensor and a second fog sensor, wherein the second fog sensor provides a second detection result, and comprises a transmitter emitting a second encoded optical signal into the vehicle's surroundings, wherein the code of the second encoded optical signal is selected among a plurality of possible codes through code selection. Thus, the first fog sensor is formed such that upon receiving the second encoded optical signal by the second optical receiver of the first fog sensor, the second encoded optical signal is decoded and analyzed by the first analyzing unit of the first fog sensor, and the detection result of the first fog sensor is provided depending on the code selection of the second encoded optical signal.

In a preferred embodiment of the system according to the present disclosure, code selection of the second encoded optical signal is done depending on the second detection result of the second fog sensor. It is preferred for the detection results to be assigned to specific fog conditions. As specific fog conditions, for example, positive detection of fog and non-detection of fog is understood. Moreover, supplemental fog conditions or detection results, respectively, specifying the above-mentioned detection results, such as detection of fog in a specified minimum distance, may be provided. Due to dependence of code selection on the detection result or fog condition, respectively, it is possible to transmit detection results from one fog sensor to another fog sensor, and hence from one vehicle to another vehicle.

For example, the analyzing unit is configured to output positive detection of fog as a first detection result, even if no first encoded optical signal is received by the associated first receiver, but a second optical signal of the second fog sensor, appropriately encoded, for example of another vehicle, is received by the first receiver. In this way, despite lack of intrinsic detection, a fog warning among vehicles may be transmitted, from a second fog sensor to a first fog sensor and eventually vice versa, for example from one vehicle to another vehicle.

Preferably, at least the first encoded optical signal is encoded as a numerical sequence, still more preferably, the first and second encoded optical signals are encoded as a numerical sequence, for example as a pseudo random numerical sequence.

According to another embodiment of the signal according to the present disclosure the second encoded optical signal comprises instruction for the first receiver, to temporarily change a receiving mode of the first receiver and/or to cause intermediate interruption of transmission of the associated first transmitter. This is for example used to facilitate and/or to expand communication between the fog sensors. For example, in this way additional information may be embedded into the second encoded optical signal, such as geographical coordinates, road information and/or time specifications, where fog was positively detected, and the first receiver may be prepared for receiving said information. For example, information obtained by travel time measurement, relating to the distance of the second fog sensor from a fog bank, is embedded into the second signal and will be communicated to the first receiver.

The present disclosure will be explained in more details by way of the following figures. The figures are to be understood only as being exemplary, thus each representing only a preferred embodiment variant, wherein.

Figure 1:
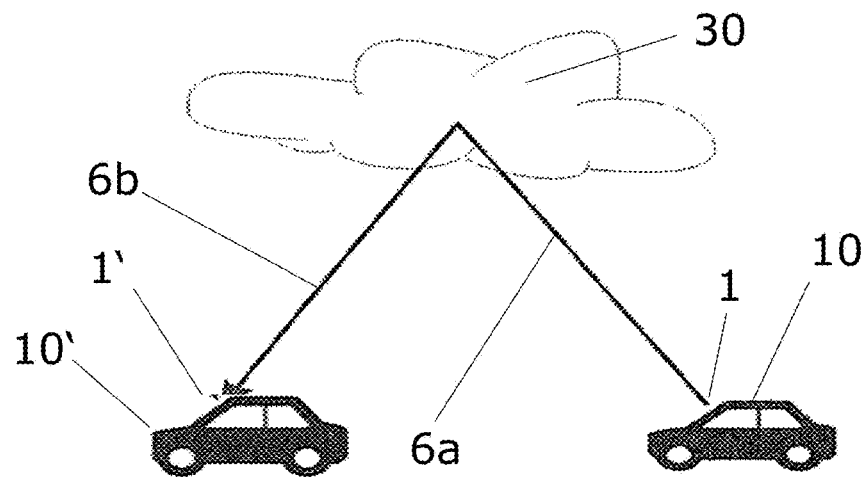
FIG. 1 shows a schematic view for illustrating the method according to the present disclosure.

The method according to the present disclosure is illustrated by way of FIG. 1, in a first embodiment. A first vehicle 10 comprises a first fog sensor 1. The fog sensor emits a first encoded optical signal 6a. The first signal 6a is reflected on a fog bank 30 located in the vehicle's surroundings and re-enters the first fog sensor 1 as a reflected signal, to therein initiate output of a fog warning to the driver. Moreover, the first encoded optical signal, as a reflected signal 6b, also reaches a second fog sensor 1' of another motor vehicle 10'.

Due to the coding of the first reflected signal 6b, this may be discriminated from an intrinsic one by the second fog sensor 1' and will not erroneously be considered as the intrinsic coming home signal thereof, i.e. as a reflected signal of the second fog sensor 1'. "Erroneously" is because, for example, the second vehicle 10', due to its distance to the fog bank 30 or due to its travel direction in relation to the fog bank 30, is not at risk of the fog 30. This problem will be solved by the method according to the present disclosure, especially the specific coding of the first signal 6a. In the present case, the transmission signals are digitally encoded, and the time sequence thereof corresponds to a set pseudo random numerical sequence, wherein herein, one among a plurality of different numerical sequences is selectable.

Figure 2:
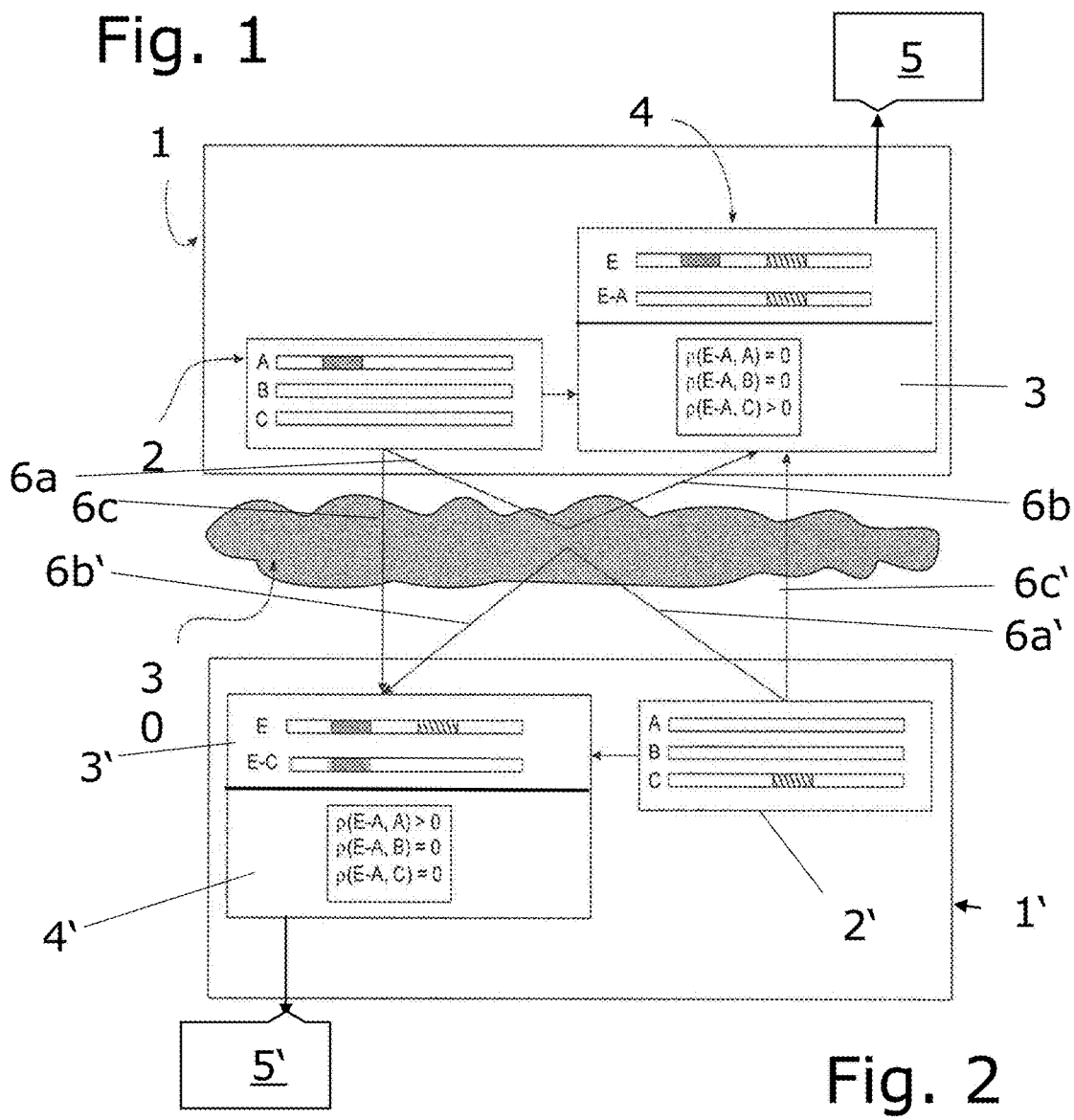
FIG. 2 shows another schematic representation for illustrating another embodiment of the method according to the present disclosure.

By way of FIG. 2, a preferred embodiment of the method according to the present disclosure is illustrated in detail. A first fog sensor 1 and a second fog sensor 1' are provided, wherein the second fog sensor 1' is equal to and is configured according to the first one. The first fog sensor 1 is for example arranged in the region of the windshield of a first vehicle not represented in detail, whereas the second fog sensor 1' is arranged in the region of the windshield of a second vehicle not represented in detail. The first fog sensor 1 comprises a first transmitter 2 and a first receiver 3. A first analyzing unit 4 associated to the first fog sensor 1 is coupled to the first receiver 3, the first analyzing unit may be provided within the first fog sensor 1, as it is shown, but alternatively, may as well be provided outside the first fog sensor 1. The first transmitter 2 of the first fog sensor 1 is capable of generating a first encoded optical signal 6a that emits into a vehicle surroundings. The first transmitter 2 is capable of coding the signal following code selection among three possible numerical codes A, B, C. After completion of code selection, the resulting code selection, herein code A, is communicated to the first receiver 3. Due to this, the first analyzing unit 4 electrically connected to the first receiver 3, following decoding the received signal 6b, which, for example, is the first encoded optical signal 6a reflected at a fog bank 30 located in the vehicle's surroundings, is to be identified by way of the coding and, upon matching of the coding, a fog warning 5 is to be emitted to the driver.

The second fog sensor 1 'accordingly comprises a second transmitter 2' and a second receiver 3'. A second analyzing unit 4' associated to the second fog sensor 1' is coupled to the second receiver 3', the second analyzing unit may be provided within the second fog sensors 1', as it is shown, but alternatively, may also be provided outside of the second fog sensor 1'. The second transmitter 2' of the second fog sensors 1' is capable of generating a second encoded optical signal 6a' that emits into a vehicle surroundings. The second transmitter 2' is capable of coding the signal following code selection among three possible numerical codes A, B, C. The result of the code selection, herein code C, will be communicated to the second receiver 3' following completion of code selection. Due to this, the second analyzing unit 4' electrically connected to the second receiver 3', following decoding the received signal 6b', which, for example, is the second encoded optical signal 6a' reflected at a fog bank 30 located in the vehicle's surroundings, is to be identified by way of the coding and, upon matching of the coding, a fog warning 5' is to be emitted to the driver.

Figure 3:
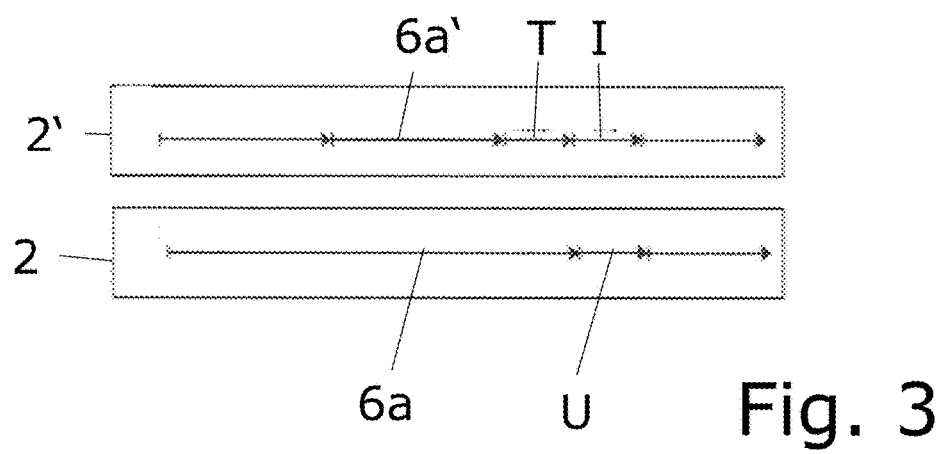
FIG. 3 shows another schematic representation for illustrating a preferred variant of the method according to the present disclosure.

Due to the different coding of the first encoded optical signal 6b and the second encoded optical signal 6b', for the respective analyzing unit in question, first analyzing unit 4 or second analyzing unit 4', the signal 6b or 6b' of the intrinsic transmitter 2 or 2', respectively, is distinguishable from the signal 6c or 6c' of the respective other transmitter 2 or 2', respectively. According to one preferred embodiment, a specific fog situation is associated to the code selection, for example, the fog situation, where no fog is present, is associated to code A, whereas to code B, the fog situation is associated, where fog has been detected, and to code C, the situation is associated, where fog is present in a set distance. In one preferred embodiment, on the first emitter 2 side and the second transmitter 2' side, code selection is done depending on of the detection result and, depending on the code selection of the respective other fog sensor 1 or 1', respectively, the detection result is provided in the form of the output 5 or 5', respectively. The information related to the respective code selection from codes A, B, C may be utilized to verify the intrinsic transmitters 2, 2' or to warn the driver, despite lacking intrinsic detection in fog detection, by an extrinsic fog sensor 1 or 1' from fog, respectively. By referring to FIG. 3, another embodiment will be illustrated, where an instruction T as well as subsequent information I is embedded into the emitted signal 6a' of a transmitter, herein often the second transmitter 2'. The instruction T is emitted on the second transmitter 2' side to put the associated first transmitter 2 into an intermediate transmission pause U for the emission of its first encoded optical signal 6a, following reception by a first receiver associated to a first transmitter 2, and to put the associated first receiver (3 in FIG. 2) and eventually the analyzing unit thereof (4 in FIG. 2) into a receiving mode, which allows transmission of the data sequence related to the respective information, embedded into the second encoded optical signal 6a'. This information may for example comprises details concerning the fog situation, but may as well comprise other traffic information, for example also information concerning the further travelling route of the vehicle.

What is claimed is:

1. A fog detection method in a vehicle, comprising:
emitting a first encoded optical signal into a vehicle's surroundings via a first fog sensor with a first transmitter;
receiving the first encoded optical signal reflected from the vehicle's surroundings via an associated first receiver;
decoding, analyzing, and providing a first detection result related to the reception of the first encoded optical signal by a first analyzing unit;
wherein for the encoding of the first encoded optical signal, a code is selected among a plurality of possible codes (A,B,C) by the first transmitter and the code selection is communicated from the first transmitter to the first receiver or to the analyzing unit, wherein in analyzing the signal received by the first receiver through the first analyzing unit, the code selection for identifying the first encoded optical signal in the received signal is used.

2. The method according to claim 1 further comprising:
emitting a second encoded optical signal into the vehicle's surroundings via a second fog sensor with a second transmitter wherein the code of the second encoded optical signal has been selected among a plurality of possible codes (A, B, C);
providing a second detection result from the second fog sensor;
receiving the second encoded optical signal by the first receiver of the first fog sensor;
decoding and analyzing the received second encoded optical signal by the first analyzing unit of the first fog sensor, wherein the detection result of the first fog sensor is provided depending on the code selection of the received second encoded optical signal.

3. The method according to claim 2, wherein the code selection of the second encoded optical signal is based on the second detection result of the second fog sensor.

4. The method according to claim 1, wherein the first encoded optical signal is encoded as a numerical sequence.

5. The method according to claim 2, wherein the second encoded optical signal comprises an instruction for the first receiver to temporarily change a receiving mode of the first receiver or an analyzing mode of the first analyzing unit or to cause intermediate interruption of transmission of the first emitter.

6. The method according to claim 2, wherein, depending on the code selection of the received second encoded optical signal, the first analyzing unit initiates output of an acoustic, haptic, or optical warning message.

7. A fog sensor comprising:
a first transmitter configured to emit a first encoded optical signal into a vehicle's surroundings;
an associated first receiver for receiving the first encoded optical signal reflected from the vehicle's surroundings; and
a first analyzing unit for decoding, analyzing, and providing a first detection result related to the reception of the first encoded optical signal;
wherein, for the encoding of the first encoded optical signal, a code is selected among a plurality of possible codes (A, B, C) by the first transmitter, and the code selection is communicated from the first transmitter to the first receiver or the analyzing unit, wherein, upon analyzing by the first analyzing unit the signal received from the first receiver, the code selection for identifying the first encoded optical signal in the received signal is used.

8. A system for fog detection, comprising:
a first fog sensor and a second fog sensor, wherein the second fog sensor provides a second detection result;
wherein the first for sensor comprises:
a first transmitter configured to emit a first encoded optical signal into a vehicle's surroundings;
an associated first receiver for receiving the first encoded optical signal reflected from the vehicle's surroundings; and
a first analyzing unit for decoding, analyzing, and providing a first detection result related to the reception of the first encoded optical signal; and
wherein, for the encoding of the first encoded optical signal, a code is selected among a plurality of possible codes (A, B, C) by the first transmitter, and the code selection is communicated from the first transmitter to the first receiver or the analyzing unit, wherein, upon analyzing by the first analyzing unit the signal received from the first receiver, the code selection for identifying the first encoded optical signal in the received signal is used;
a transmitter emitting a second encoded optical signal into the vehicle's surroundings, wherein the code of the second encoded optical signal was selected among a plurality of possible codes (A, B, C), wherein the first fog sensor is formed such that following reception of the second encoded optical signal by the first receiver of the first fog sensor, the received second encoded optical signal is decoded and analyzed by the first analyzing unit of the first fog sensor, and the detection result of the first fog sensor is provided depending on the code selection of the received second encoded optical signal.

9. The system of claim 8, wherein the code selection of the second encoded optical signal is based on the second detection result of the second fog sensor.

10. The system of claim 8, wherein at least the first encoded optical signal is encoded as a numerical sequence.

11. The system of claim 8, wherein the second encoded optical signal comprises an instruction for the first receiver to temporarily change a receiving mode of the first receiver or an analyzing mode of the first analyzing unit or to cause intermediate interruption of transmission of the first emitter.

* * * * *